US009303290B2

(12) United States Patent
Fedurco et al.

(10) Patent No.: US 9,303,290 B2
(45) Date of Patent: *Apr. 5, 2016

(54) METHOD OF NUCLEOTIDE DETECTION

(71) Applicant: Illumina Cambridge Limited, Essex (GB)

(72) Inventors: Milan Fedurco, Essex (GB); Anthony Romieu, Essex (GB); Gerardo Turcatti, Essex (GB)

(73) Assignee: Illumina Cambridge Limited, Nr Saffron Walden, Essex ( * ) Notice: Subject to any disclaimer, the term of this patent is extended or adjusted under 35 U.S.C. 154(b) by 43 days.

This patent is subject to a terminal disclaimer.

(21) Appl. No.: 14/295,039

(22) Filed: Jun. 3, 2014

(65) Prior Publication Data

US 2014/0378323 A1     Dec. 25, 2014

Related U.S. Application Data

(63) Continuation of application No. 11/792,878, filed as application No. PCT/GB2005/004776 on Dec. 13, 2005.

(30) Foreign Application Priority Data

Dec. 13, 2004  (GB) .................................. 0427236.5
Jul. 20, 2005  (GB) .................................. 0514933.1

(51) Int. Cl.
*C12Q 1/68* (2006.01)
*C12P 19/36* (2006.01)
*C07H 21/02* (2006.01)

(52) U.S. Cl.
CPC ............ *C12Q 1/6874* (2013.01); *C12Q 1/6869* (2013.01)

(58) Field of Classification Search
CPC ............................ C12Q 1/6874; C12Q 1/6869
USPC .................................. 435/6.1, 91.1; 506/23.1
See application file for complete search history.

(56) References Cited

U.S. PATENT DOCUMENTS

| 6,544,797 | B1 | 4/2003 | Buechler et al. |
| 2002/0006622 | A1 | 1/2002 | Bradley et al. |
| 2004/0241742 | A1 | 12/2004 | Peck et al. |
| 2004/0241880 | A1 | 12/2004 | Leproust et al. |

FOREIGN PATENT DOCUMENTS

| WO | 94/02638 | 2/1994 |
| WO | 97/18328 | 5/1997 |
| WO | 98/35012 | 8/1998 |
| WO | 98/45705 | 10/1998 |
| WO | 00/06770 | 2/2000 |
| WO | 00/18957 | 4/2000 |
| WO | 00/70073 | 11/2000 |
| WO | 01/94630 | 12/2001 |
| WO | 02/086145 | 10/2002 |
| WO | 03/048387 | 6/2003 |
| WO | 2004/018493 | 3/2004 |
| WO | 2004/108966 | 12/2004 |
| WO | 2005/004025 | 10/2005 |

OTHER PUBLICATIONS

EP Decision to Grant, "Application No. 05818529.9", Dated Nov. 2, 2012.
EP Office Action, "Application No. 05818529.9", Dated Dec. 8, 2010.
"Communication of a further submission on behalf of Opponent filed in EP Appl. No. 05818529.9", Jun. 18, 2014.
"Communication of a Notice of Opposition issued for EP Appl. No. 05818529.9", Aug. 28, 2013, 27 pages.
"Declaration Under 37 C.F.R. 1.132 by Kay Klausing", U.S. Appl. No. 11/792,878, Mar. 14, 2012, 1-6.
"ProLong Antifade Kit *P7481) Handbook", Molecular Probes Product Information, Mar. 28, 2005, 1-3.
Akerman, et al., "Single- and double-strand photocleavage of DNA by YO, YOYO and TOTO", Nucleic Acids Research, vol. 24, No. 6, 1996, 1080-1090.
Bernas, et al., "Minimizing photobleaching during confocal microscopy of flourescent probes bound to chromatin: role of anoxia and photon flux", Journal of Microscopy, vol. 215, Sep. 3, 2004, 281-296.
Dittrich, et al., "Photbleaching and stabilization of fluorophores used for single-molecule analysis with one- and two-photon excitation", Applied Physics B, 73, 2001, 829-837.
Giangiacomo, et al., "Ascorbic acid and glucose oxidation by ultraviolet A-generated oxygen free radicals", Investigative Opthamology and Visual Science, 37, 1996, 1549-1556.
Kapanidis, et al., "Fluorescent probes and bioconjugation chemistries for single-molecule fluorescene analysis of biomolecules", Journal of Chemical Physics, vol. 17, No. 24, Dec. 22, 2002, 10953-10964.
Mitra, et al., "Fluorescent in situ sequencing on polymerase colonies", Analytical Biochemistry, Academic Press, San Diego US vol. 320 No. 1, 2002, 55-65.
Mitra, Robi D. et al., "Fluorescent in situ sequencing on polymerase colonies", Analytical Biochemistry—320 (2003) 55-65, 2003, 55-65.
Olson, et al., "Electrophoresis of DNA Absorbed to a Cationic Supported Bilayer", Langmuir, vol. 17, Dec. 10, 2001, 7396-7401.
Sakagami, et al., "The interaction between two antioxidants, sodium ascorbate and gallic acid: radical intensity and apoptosis induction", Anticancer Res., 16(3A), 1996, 1231-1234.
Tsien, Roger Y et al., "Fluorophores for Confocal Microscopy", Handbook of Biological Confocal Microscopy, 2nd edition, edited by James B. Fawley, 1995, 267-269.
Vigers, et al., "Fluorescent microtubules break up under illumination", The Journal of Cell Biology, vol. 107, Sep. 1, 1988, 1011-1024.
Weinbauer, et al., "Utility of green fluorescent nucleic acid dyes and aluminum oxide membrane filters for rapid epifluorescence enumeration of soil and sediment bacteria", Applied and Environmental Microbiology, vol. 64, No. 12, Dec. 1998, 5000-5003.

*Primary Examiner* — Sharmila G. Landau
*Assistant Examiner* — Shannon Janssen
(74) *Attorney, Agent, or Firm* — Brent C. Moore; Illumina, Inc.

(57) ABSTRACT

The invention relates to an additive which can be added to buffers used in nucleotide detection processes and improved methods of nucleic acid sequencing using this additive. In particular the invention relates to use of the additive to improve the efficiency of fluorescence-based multiple cycle nucleic acid sequencing reactions.

15 Claims, 2 Drawing Sheets

Template with Lambda F fragment

```
P7 primer
NH2-CAAGCAGAAG ACGGCATACG ATCCGACAGC TT>
    CAAGCAGAAG ACGGCATACG ATCCGACAGC AGC TTTATGAAAA TAATCTCCAC TGCCCGCTTT CCAGTCGGGA AACCTGTCGT
    GTTCGTCTTC TGCCGTATGC TAGGCTGTCG AAATACTTTT ATTAGAGGTG ACGGGCGAAA GGTCAGCCCT TTGGACAGCA
                                                <GTG ACGGGCGAAA GGTCAGCCCT TTGGACAGCA GCCAGCTGCA TTAATGAATC GGCCAACGCG CGGGGAGAGG CGGTTTGCGT ATTGGGCGCT CTTCCGCTTC CTCGCTCACT
    CGGTCGACGT AATTACTTAG CCGGTTGCGC GCCCCTCTCC GCCAAACGCA TAACCCGCGA GAAGGCGAAG GAGCGAGTGA
    CGGTC Sequencing primer #562

GACTCGCTGC GCTCGGTCGT TCGGCTGCGG CGAGCGGTAT CAGCTCACTC AAAGGCGGTA ATACGGTTAT CCACAGAATC
    CTGAGCGACG CGAGCCAGCA AGCCGACGCC GCTCGCCATA GTCGAGTGAG TTTCCGCCAT TATGCCAATA GGTGTCTTAG

AGGGGATAAC GCAGGAAAGA ACATGTGAGC AAAAGGCCAG CAAAAAGGCCA GGAACCGTAA AAAGGCCGCG TTGCTGGCGT
    TCCCCTATTG CGTCCTTTCT TGTACACTCG TTTTCCGGTC GTTTTCCGGT CCTTGGCATT TTTCCGGCGC AACGACCGCA

TTTTCTCGGT GGTCGCCGTA TCATT
    AAAAGAGCCA CCAGCGGCAT AGTAA
    AAAAGAGCCA CCAGCGGGCAT AGTAA-SS-NH2     P5 primer               <GC AACGACCGCA
```

FIG. 1

SEQUENCE LISTING

```
<160> NUMBER OF SEQ ID NOS: 6

<210> SEQ ID NO 1
<211> LENGTH: 31
<212> TYPE: DNA
<213> ORGANISM: Artificial sequence
<220> FEATURE:
<223> OTHER INFORMATION: Synthetic primer

<400> SEQUENCE: 1 ttttttttt caagcagaag acggcatacg a                                     31

<210> SEQ ID NO 2
<211> LENGTH: 33
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LICATION: (11)..(13)
<223> OTHER INFORMATION: diol linker

<400> SEQUENCE: 2 ttttttttt nnnaatgata cggcgaccac cga                                   33

<210> SEQ ID NO 3
<211> LENGTH: 32
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: contains -NH2 tail

<400> SEQUENCE: 3
caagcagaag acggcatacg atccgacagc tt                                   32
```

```
<210> SEQ ID NO 4
<211> LENGTH: 38
<212> TYPE: DNA
<213> ORGANISM: Artificial sequence
<220> FEATURE:
<223> OTHER INFORMATION: Synthetic primer

<400> SEQUENCE: 4
ctggcacgac aggtttcccg actggaaagc gggcagtg                           38

<210> SEQ ID NO 5
<211> LENGTH: 37
<212> TYPE: DNA
<213> ORGANISM: Artificial sequnence
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: SS-NH2 tail

<400> SEQUENCE: 5
aatgatacgg cgaccaccga gaaaaacgcc agcaacg                            37

<210> SEQ ID NO 6
<211> LENGTH: 345
<212> TYPE: DNA
<213> ORGANISM: Artificial sequence
<220> FEATURE:
<223> OTHER INFORMATION: Synthetic sequence

<400> SEQUENCE: 6
caagcagaag acggcatacg atccgacagc tttatgaaaa taatctccac tgcccgcttt    60
ccagtcggga aacctgtcgt gccagctgca ttaatgaatc ggccaacgcg cggggagagg   120
cggtttgcgt attgggcgct cttccgcttc ctcgctcact gactcgctgc gctcggtcgt   180
tcggctgcgg cgagcggtat cagctcactc aaaggcggta atacggttat ccacagaatc   240
aggggataac gcaggaaaga acatgtgagc aaaaggccag caaaaggcca ggaaccgtaa   300
aaaggccgcg ttgctggcgt ttttctcggt ggtcgccgta tcatt                  345
```

METHOD OF NUCLEOTIDE DETECTION

FIELD OF THE INVENTION

The invention relates to an additive which can be added to buffers used in nucleotide detection processes and improved methods of nucleic acid sequencing using this additive. In particular the invention relates to use of the additive to improve the efficiency of fluorescence-based multiple cycle nucleic acid sequencing reactions.

BACKGROUND TO THE INVENTION

There are known in the art methods of nucleic acid sequencing based on successive cycles of incorporation of fluorescently labelled nucleic acid analogues. In such "sequencing by synthesis" or "cycle sequencing" methods the identity of the added base is determined after each nucleotide addition by detecting the fluorescent label.

In particular, U.S. Pat. No. 5,302,509 describes a method for sequencing a polynucleotide template which involves performing multiple extension reactions using a DNA polymerase or DNA ligase to successively incorporate labelled polynucleotides complementary to a template strand. In such a "sequencing by synthesis" reaction a new polynucleotide strand based-paired to the template strand is built up in the 5' to 3' direction by successive incorporation of individual nucleotides complementary to the template strand. The substrate nucleoside triphosphates used in the sequencing reaction are labelled at the 3' position with different 3' labels, permitting determination of the identity of the incorporated nucleotide as successive nucleotides are added.

The present inventors have developed methods of sequencing multiple nucleic acid molecules in parallel based on the use of arrays, wherein multiple template molecules immobilised on the array are sequenced in parallel. Such arrays may be single molecule arrays or clustered arrays.

The inventors have observed that when performing sequencing-by-synthesis using fluorescently labelled nucleotide analogues the brightness of the incorporated fluorophore diminishes at each cycle of nucleotide addition. This is a particular problem when sequencing nucleic acid templates on arrays, and more particularly arrays comprised of clusters of surface-bound DNA. Cycles of sequencing may stop at around cycle 8-10 due to loss of signal from the fluorescently labelled nucleotide analogue incorporated into extended strand complementary to the template, making it difficult to score accurately the identity of the incorporated base. Moving to a new area of the array that has not been previously scanned however clearly shows that the correct base can be accurately read. This is indicative of light-induced damage to the nucleic acid templates upon repeated exposures to the intense illumination used to read the incorporated fluorophores.

It is known in the art to add chemical antioxidants such as ascorbic acid (vitamin C) to fluorescent imaging buffers. It has, however, never previously been suggested to add such antioxidants to buffers used for detection/imaging of fluorophores incorporated in or attached to nucleic acid. More particularly, it has never previously been suggested to use antioxidants such as ascorbate as additives in buffers used for imaging of arrays during cycles of nucleic acid sequencing.

The inventors have now observed that the presence of one or more antioxidants in buffers used in any molecular biology technique requiring detection of a fluorescent moiety incorporated in or attached to a nucleic acid, which detection includes repeated or prolonged exposure to intense illumination, is surprisingly advantageous.

DESCRIPTION OF THE INVENTION

In a first aspect the invention provides a method of detecting a fluorescent moiety incorporated in or attached to a polynucleotide molecule, wherein the method includes a detection step which requires repeated or prolonged exposure to intense illumination, and wherein detection of the fluorescent moiety is carried out in a buffer which comprises one or more antioxidants.

The invention will now be further described. In the following passages different features of the invention are defined in more detail. Each feature so defined may be combined with any other feature or features unless clearly indicated to the contrary. In particular any feature indicated as being preferred or advantageous may be combined with any other feature or features indicated as being preferred or advantageous.

The method of the invention is useful in many techniques requiring incorporation of a fluorescently labeled nucleotide into a polynucleotide, including but not limited to sequencing reactions, polynucleotide synthesis, nucleic acid amplification, nucleic acid hybridisation assays, single nucleotide polymorphism studies, and other such techniques. All such uses and methods utilizing the buffer additives of the invention in the imaging/detection steps are included within the scope of the present invention.

Preferably the method is a sequencing reaction, particularly a sequencing-by-synthesis reaction. In particular the method of invention is of particular utility in a method of sequencing a template nucleic acid comprising incorporating one or more fluorescently labelled nucleotides into a strand of nucleic acid complementary to said template nucleic acid and determining the identity of the base present in one or more of the incorporated nucleotide(s), wherein the step of determining the identity of the base present in the incorporated nucleotide(s) is carried out in a buffer which comprises one or more antioxidants.

The subsequent discussion shall focus mainly on sequencing-by-synthesis reactions although it is to be understood that the invention should not be considered as so limited.

Use of a buffer which comprises one or more antioxidants in such methods substantially improves performance, increasing the number of nucleotide additions which can be accurately determined in each sequencing experiment. The inclusion of an antioxidant as an additive in the buffer prevents the loss of signal that otherwise occurs over successive cycles of nucleotide incorporation and allows more cycles of sequencing to be achieved using the same sequencing templates.

Preferably at least one of the one or more antioxidants is ascorbic acid or a salt, analogue, or derivative thereof.

Unless otherwise stated the terms "ascorbate" and "ascorbic acid" as used herein refer to both the L-isomer and the D-isomer, and mixtures, including racemic mixtures, thereof. Both optical isomers are capable of functioning as antioxidants.

A preferred salt includes sodium ascorbate, e.g. sodium L-ascorbate.

There are known in the art numerous ascorbate analogues and derivatives having antioxidant activity which can be used in the method of the invention. Suitable derivatives and analogues include those in which the 5- and/or 6-hydroxy group is esterified or otherwise derivatised. Alternatively, the 5- and/or 6-hydroxy group may be replaced with an alternative functional group, such as halo or amino. Other alternative derivatives are those in which the 5- and/or 6-hydroxy group is absent and (i.e with a hydrogen atom in place of the hydroxyl group). Representative examples of such derivatives include, but are not limited to, 6-O-tosyl-L-ascorbate, 5-deoxy-L-ascorbate, 6-bromo-6-deoxy-L-ascorbate, 6-amino-6-deoxy-L-ascorbate, L-ascorbic acid 6-carboxylate, and 6-O-ascorbyl alkanoates such as 6-ascorbyl palmitate (palmitoyl ascorbate).

Advantageously a combination of two or more antioxidants may be present in the buffer. Preferably, at least one of the antioxidants in such combinations is ascorbic acid or a salt, analogue, or derivative thereof as discussed immediately hereinbefore Preferably the one or more antioxidants will be present in the buffer at a concentration of at least 10 mM, preferably at least 20 mM. Whilst there is no particular upper limit, generally a concentration of 100 mM, more particularly a concentration of 50 mM, represents a preferable upper limit to the concentration of antioxidant present. For example, therefore, the one or more antioxidants may be present in the buffer at a concentration in the range of from 10 to 100 mM, preferably 20 to 50 mM, more preferably about 50 mM.

The pH of the buffer is not of critical importance; the invention may be operated at a fairly broad pH range. Generally, however, broadly neutral pH ranges are appropriate for the buffers, such as from about pH 5 to about pH 9, preferably from pH 5.5 to 8.6, e.g. about pH 7.

The nature of the buffering agent itself is likewise not of any great importance: any buffering agent may be used. An example of an appropriate, indeed a preferred convenient buffering agent is tris (tris (hydroxymethyl)aminomethane). Additionally salts, e.g. sodium chloride or any other convenient salt, for example present at a concentration in the range of from 5-100 mM, preferably 10-70 mM, and particularly 30 mM, may be present.

An example of a particularly preferred buffer which may be used in all aspects of the invention comprises Tris (100 mM), NaCl (30 mM), sodium ascorbate (50 mM) at pH 7.

The nucleotide(s) incorporated into the strand of nucleic acid complementary to the template nucleic are each fluorescently labelled. The inclusion of a fluorescent label facilitates detection/identification of the base present in the incorporated nucleotide(s). Appropriate fluorophores are well known in the art.

The labels may be the same for each type of nucleotide, or each nucleotide type may carry a different label. This facilitates the identification of incorporation of a particular nucleotide. Thus, for example modified adenine, guanine, cytosine and thymine would all have attached a different fluorophore to allow them to be discriminated from one another readily. When sequencing on arrays, a mixture of labelled and unlabelled nucleotides may be used.

Detectable labels such as fluorophores can be linked to nucleotides via the base using a suitable linker. The linker may be acid labile, photolabile or contain a disulfide linkage. Preferred labels and linkages include those disclosed in WO03/048387. Other linkages, in particular phosphine-cleavable azide-containing linkers, may be employed in the invention as described in greater detail in WO2004/018493. The contents of WO 03/048387 and WO 2004/018493 are incorporated herein in their entirety by reference.

The nucleotides described in WO2004/018493 comprise a purine or pyrimidine base and a ribose or deoxyribose sugar moiety which has a removable blocking group covalently attached thereto, preferably at the 3'O position. 3' blocking groups are also described in WO2004/018497, the contents of which is also incorporated herein in its entirety by reference.

Use of such 3'-blocked nucleotides permits controlled incorporation of nucleotides in a step-wise manner, since the presence of a blocking group at the 3'-OH position prevents incorporation of additional nucleotides. The detectable label may, if desirable, be incorporated into the blocking groups as is disclosed in WO2004/018497.

Methods for detecting fluorescently labelled nucleotides generally require use of incident light (e.g. laser light) of a wavelength specific for the fluorescent label, or the use of other suitable sources of illumination, to excite the fluorophore. Fluorescent light emitted from the fluorophore may then be detected at the appropriate wavelength using a suitable detection system such as for example a Charge-Coupled-Device (CCD) camera, which can optionally be coupled to a magnifying device, a fluorescent imager or a confocal microscope.

If sequencing is carried out on an array, detection of an incorporated base may be carried out by using a confocal scanning microscope to scan the surface of the array with a laser, to image fluorescent labels attached to the incorporated nucleotide(s). Alternatively, a sensitive 2-D detector, such as a charge-coupled detector (CCD), can be used to visualise the signals generated. This technique is particularly useful with single molecule arrays. Other techniques such as scanning near-field optical microscopy (SNOM) are available and may be used when imaging dense arrays. For a description of scanning near-field optical microscopy, see Moyer et al., Laser Focus World 29:10, 1993. An additional technique that may be used is surface-specific total internal reflection fluorescence microscopy (TIRFM); see, for example, Vale et al., Nature, (1996) 380: 451-453). Suitable apparatus used for imaging polynucleotide arrays are known in the art and the technical set-up will be apparent to the skilled person.

Detection buffers containing antioxidants, such as sodium ascorbate, show a clear improvement (over corresponding buffers absent such antioxidants) at preventing light-induced chemical artefacts in cycles of sequencing-by-synthesis based on detection of fluorescently labelled nucleotide analogues. The inclusion of antioxidants prevents/reduces light-induced chemical reactions from damaging the integrity of the nucleic acid template and allows accurate determination of the identity of the incorporated base over at least 2, preferably at least 10, and more preferably at least 16 cycles of nucleotide incorporation. Preferably from 10 to 30 and more preferably from 16 to 30 nucleotides are successively incorporated, and identified, in the sequencing reaction.

The ability to accurately sequence 10 or more, and preferably 16 or more, consecutive nucleotides in a sequencing reaction is a significant advantage in applications such as genome re-alignment.

In the context of this invention the terms "sequencing reaction", "sequencing methodology" or "method of sequencing" generally refer to any polynucleotide "sequencing-by-synthesis" reaction which involves sequential addition of one or more nucleotides to a growing polynucleotide chain in the 5' to 3' direction using a polymerase in order to form an extended polynucleotide chain complementary to the template nucleic acid to be sequenced. The identity of the base present in one or more of the added nucleotide(s) is determined in a detection or "imaging" step. The identity of the added base is preferably determined after each nucleotide incorporation step. The sequence of the template may then be inferred using conventional Watson-Crick base-pairing rules. For the avoidance of doubt "sequencing" can also encompass incorporation and identification of a single nucleotide. Determination of the identity of a single base may be useful, for example, in the scoring of single nucleotide polymorphisms.

The nucleic acid template to be sequenced in a sequencing reaction may be any polynucleotide that it is desired to sequence. The nucleic acid template for a sequencing reaction will typically comprise a double-stranded region having a free 3' hydroxyl group which serves as a primer or initiation point for the addition of further nucleotides in the sequencing reaction. The region of the template to be sequenced will overhang this free 3' hydroxyl group on the complementary strand. The primer bearing the free 3' hydroxyl group may be added as a separate component (e.g. a conventional oligonucleotide sequencing primer) which hybridises to a region of the template to be sequenced. Alternatively, the primer and the template strand to be sequenced may each form part of a partially self-complementary nucleic acid strand capable of forming an intramolecular duplex, such as for example a hairpin loop structure. Nucleotides are added successively to the free 3' hydroxyl group, resulting in synthesis of a polynucleotide chain in the 5' to 3' direction. After each nucleotide addition the nature of the base which has been added may be determined, thus providing sequence information for the nucleic acid template.

The term "incorporation" of a nucleotide into a nucleic acid strand (or polynucleotide) refers to joining of the nucleotide to the free 3' hydroxyl group of the nucleic acid strand via formation of a phosphodiester linkage with the 5' phosphate group of the nucleotide.

The nucleic acid template to be sequenced may be DNA or RNA, or even a hybrid molecule comprised of deoxynucleotides and ribonucleotides. The nucleic acid may comprise naturally occurring and/or non-naturally occurring nucleotides and natural or non-natural backbone linkages.

Nucleic acid templates to be sequenced may be attached to a solid support via any suitable linkage method known in the art. Preferably linkage will be via covalent attachment. If the templates are "arrayed" on a solid support then the array may take any convenient form. Thus, the method of the invention is applicable to all types of "high density" arrays, including single-molecule arrays and clustered arrays.

When referring to immobilisation of molecules (e.g. nucleic acids) to a solid support, the terms "immobilised" and "attached" are used interchangeably herein and both terms are intended to encompass direct or indirect, covalent or non-covalent attachment, unless indicated otherwise, either explicitly or by context. In certain embodiments of the invention covalent attachment may be preferred, but generally all that is required is that the molecules (e.g. nucleic acids) remain immobilised or attached to the support under the conditions in which it is intended to use the support, for example in applications requiring nucleic acid amplification and/or sequencing.

Certain embodiments of the invention may make use of solid supports comprised of an inert substrate or matrix (e.g. glass slides, polymer beads etc) which is been "functionalised", for example by application of a layer or coating of an intermediate material comprising reactive groups which permit covalent attachment to biomolecules, such as polynucleotides. Examples of such supports include, but are not limited to, polyacrylamide hydrogels supported on an inert substrate such as glass, particularly polyacrylamide hydrogels as described in WO 2005/065814, the contents of which are incorporated herein in their entirety by reference. In such embodiments, the biomolecules (e.g. polynucleotides) may be directly covalently attached to the intermediate material (e.g. the hydrogel) but the intermediate material may itself be non-covalently attached to the substrate or matrix (e.g. the glass substrate). The term "covalent attachment to a solid support" is to be interpreted accordingly as encompassing this type of arrangement.

The method of the invention may be used for sequencing on essentially any type of array formed by immobilisation of nucleic acid molecules on a solid support, and more particularly any type of high-density array. However, the method of the invention is particularly advantageous in the context of sequencing on clustered arrays.

In multi-polynucleotide or clustered arrays distinct regions on the array comprise multiple polynucleotide template molecules. Depending on how the array is formed each site on the array may comprise multiple copies of one individual polynucleotide molecule or even multiple copies of a small number of different polynucleotide molecules (e.g. multiple copies of two complementary nucleic acid strands).

Multi-polynucleotide or clustered arrays of nucleic acid molecules may be produced using techniques generally known in the art. By way of example, WO 98/44151 and WO 00/18957 both describe methods of solid-phase nucleic acid amplification which allow amplification products to be immobilised on a solid support in order to form arrays comprised of clusters or "colonies" of immobilised nucleic acid molecules. Each cluster or colony on such an array is formed from a plurality of identical immobilised polynucleotide strands and a plurality of identical immobilised complementary polynucleotide strands. The arrays so-formed are generally referred to herein as "clustered arrays". The nucleic acid molecules present on the clustered arrays prepared according to these methods are suitable templates for sequencing using the method of the invention. However, the invention is not intended to use of the method in sequencing reactions carried out on clustered arrays prepared according to these specific methods.

The products of solid-phase amplification reactions such as those described in WO 98/44151 and WO 00/18957 are so-called "bridged" structures formed by annealing of pairs of immobilised polynucleotide strands and immobilised complementary strands, both strands being immobilised on the solid support at the 5' end, preferably via a covalent attachment. In order to improve the performance of sequencing on arrays comprised of such bridged structures it is preferred to remove substantially all or at least a portion of one of the immobilised strands in the "bridged" structure in order to generate a template which is at least partially single-stranded. The portion of the template which is single-stranded will thus be available for hybridisation to a sequencing primer. The process of removing all or a portion of one immobilised strand in a "bridged" double-stranded nucleic acid structure may be referred to herein as "linearisation".

It is known in the art that bridged template structures may be linearised by cleavage of one or both strands with a restriction endonuclease and this method of linearisation may be used in the context of the invention. A disadvantage of the use of restriction enzymes for linearisation is that it requires the presence of a specific recognition sequence for the enzyme at a suitable location in the bridged template structure. There is a risk that the same recognition sequence may appear elsewhere in the bridged structure, meaning that the enzyme may cut at one or more further sites, in addition to the intended cleavage site for linearisation. This may be a particular problem where the bridged structures to be linearised are derived by solid-phase amplification of templates of unknown or partially unknown sequence, since it cannot be predicted in advance whether a particular enzyme will cut within the region of unknown sequence.

The inventors have developed a number of alternative cleavage methods for template linearisation which do not require the use of restriction enzymes, as described below. Any of these methods can be used for linearisation of "bridged" nucleic acid structures in clustered arrays formed by solid-phase amplification, and indeed for linearisation any "bridged" double-stranded nucleic acid molecule formed by annealing of complementary polynucleotide strands that are attached to a solid support at the 5' end, whether or not formed by solid-phase amplification.

Therefore, another aspect the invention provides a method of generating a template for a nucleic acid sequencing reaction comprising,
(i) providing at least one double-stranded nucleic acid molecule, wherein both strands of the double-stranded nucleic acid molecule are attached to the solid support at the 5' end,
(ii) cleaving one or both strands of the double-stranded nucleic acid molecule, and
(iii) subjecting the cleaved strand(s) to denaturing conditions to remove the portion of the cleaved strand(s) not attached to the solid support, thereby generating a partially or substantially single-stranded template for a nucleic acid sequencing reaction,
characterised in that step (ii) does not comprise cleavage with a restriction endonuclease or a nicking endonuclease.

In step (i) the double-stranded nucleic acid molecule is typically a bridged nucleic acid structure produced by a solid-phase nucleic acid amplification method.

In one embodiment cleavage may occur at a cleavage site in one or both strands of the double-stranded nucleic acid molecule which comprises one or more or any combination of non-natural nucleotides, ribonucleotides or a non-nucleotide chemical modifications.

Preferred cleavage methods are as follows:
i) Chemical Cleavage

The term "chemical cleavage" encompasses any method which utilises a non-nucleic acid and non-enzymatic chemical reagent in order to promote/achieve cleavage of one or both strands of a double-stranded nucleic acid molecule. If required, one or both strands of the double-stranded nucleic acid molecule may include one or more non-nucleotide chemical moieties and/or non-natural nucleotides and/or non-natural backbone linkages in order to permit chemical cleavage reaction. In a preferred embodiment the modification(s) required to permit chemical cleavage may be incorporated into an amplification primer used in solid-phase nucleic acid amplification.

In a preferred but non-limiting embodiment one strand of the double-stranded nucleic acid molecule (or the amplification primer from which this strand is derived if formed by solid-phase amplification) may include a diol linkage which permits cleavage by treatment with periodate (e.g. sodium periodate). It will be appreciate that more than one diol can be included at the cleavage site.

Diol linker units based on phosphoramidite chemistry suitable for incorporation into polynucleotide chains are commercially available from Fidelity systems Inc. (Gaithersburg, Md., USA). One or more diol units may be incorporated into a polynucleotide using standard methods for automated chemical DNA synthesis. Hence, oligonucleotide primers including one or more diol linkers can be conveniently prepared by chemical synthesis.

In order to position the diol linker at an optimum distance from the solid support one or more spacer molecules may be included between the diol linker and the site of attachment to the solid support. The spacer molecule may be a non-nucleotide chemical moiety. Suitable spacer units based on phosphoramidite chemistry for use in conjunction with diol linkers are also supplied by Fidelity Systems Inc. One suitable spacer for use with diol linkers is the spacer denoted arm 26, identified in the accompanying examples. To enable attachment to a solid support at the 5' end of the polynucleotide strand arm 26 may be modified to include a phosphorothioate group. The phosphorothioate group can easily be attached during chemical synthesis of a "polynucleotide" chain including the spacer and diol units.

Other spacer molecules could be used as an alternative to arm 26. For example, a stretch of non-target "spacer" nucleotides may be included. Typically from 1 to 20, more preferably from 1 to 15 or from 1 to 10, and more particularly 2, 3, 4, 5, 6, 7, 8, 9 or 10 spacer nucleotides may be included. Most preferably 10 spacer nucleotides will be positioned between the point of attachment to the solid support and the diol linker. It is preferred to use polyT spacers, although other nucleotides and combinations thereof can be used. In one preferred embodiment the primer may include 10T spacer nucleotides.

The diol linker is cleaved by treatment with a "cleaving agent", which can be any substance which promotes cleavage of the diol. The preferred cleaving agent is periodate, preferably aqueous sodium periodate ($NaIO_4$). Following treatment with the cleaving agent (e.g. periodate) to cleave the dial, the cleaved product may be treated with a "capping agent" in order to neutralise reactive species generated in the cleavage reaction. Suitable capping agents for this purpose include amines, such as ethanolamine. Advantageously, the capping agent (e.g. ethanolamine) may be included in a mixture with the cleaving agent (e.g. periodate) so that reactive species are capped as soon as they are formed.

The combination of a diol linkage and cleaving agent (e.g. periodate) to achieve cleavage of one strand of a double-stranded nucleic acid molecule is preferred for linearisation of nucleic acid molecules on solid supported polyacrylamide hydrogels because treatment with periodate is compatible with nucleic acid integrity and with the chemistry of the hydrogel surface. However, utility of diol linkages/periodate as a method of linearisation is not limited to polyacrylamide hydrogel surfaces but also extends to linearisation of nucleic acids immobilised on other solid supports and surfaces, including supports coated with functionalised silanes (etc).

In a further embodiment, the strand to be cleaved (or the amplification primer from which this strand is derived if prepared by solid-phase amplification) may include a disulphide group which permits cleavage with a chemical reducing agent, e.g. Tris (2-carboxyethyl)-phosphate hydrochloride (TCEP).

ii) Cleavage of Abasic Sites in a Double-Stranded Molecule

An "abasic site" is defined as a nucleoside position in a polynucleotide chain from which the base component has been removed. Abasic sites can occur naturally in DNA under physiological conditions by hydrolysis of nucleoside residues, but may also be formed chemically under artificial conditions or by the action of enzymes. Once formed, abasic sites may be cleaved (e.g. by treatment with an endonuclease or other single-stranded cleaving enzyme, exposure to heat or alkali), providing a means for site-specific cleavage of a polynucleotide strand.

In a preferred but non-limiting embodiment an abasic site may be created at a pre-determined position on one strand of a double-stranded polynucleotide and then cleaved by first incorporating deoxyuridine (U) at a pre-determined cleavage site in one strand of the double-stranded nucleic acid molecule. This can be achieved, for example, by including U in one of the primers used for preparation of the double-stranded nucleic acid molecule by solid-phase PCR amplification. The enzyme uracil DNA glycosylase (UDG) may then be used to remove the uracil base, generating an abasic site on one strand. The polynucleotide strand including the abasic site may then be cleaved at the abasic site by treatment with endonuclease (e.g EndoIV endonuclease, AP lyase, FPG glycosylase/AP lyase, EndoVIII glycosylase/AP lyase), heat or alkali.

Abasic sites may also be generated at non-natural/modified deoxyribonucleotides other than deoxyuridine and cleaved in an analogous manner by treatment with endonuclease, heat or alkali. For example, 8-oxo-guanine can be converted to an abasic site by exposure to FPG glycosylase. Deoxyinosine can be converted to an abasic site by exposure to AlkA glycosylase. The abasic sites thus generated may then be cleaved, typically by treatment with a suitable endonuclease (e.g. EndoIV, AP lyase). If the non-natural/modified nucleotide is to be incorporated into an amplification primer for use in solid-phase amplification, then the non-natural/modified nucleotide should be capable of being copied by the polymerase used for the amplification reaction.

In one embodiment, the molecules to be cleaved may be exposed to a mixture containing the appropriate glycosylase and one or more suitable endonucleases. In such mixtures the glycosylase and the endonuclease will typically be present in an activity ratio of at least about 2:1.

This method of cleavage has particular advantages in relation to the creation of templates for nucleic acid sequencing. In particular, cleavage at an abasic site generated by treatment with a glycosylase such as UDG generates a free 3' hydroxyl group on the cleaved strand which can provide an initiation point for sequencing a region of the complementary strand. Moreover, if the starting double-stranded nucleic acid contains only one cleavable (e.g. uracil) base on one strand then a single "nick" can be generated at a unique position in this strand of the duplex. Since the cleavage reaction requires a residue, e.g. deoxyuridine, which does not occur naturally in DNA, but is otherwise independent of sequence context, if only one non-natural base is included there is no possibility of glycosylase-mediated cleavage occurring elsewhere at unwanted positions in the duplex. In contrast, were the double-stranded nucleic acid to be cleaved with a "nicking" endonuclease that recognises a specific sequence, there is a possibility that the enzyme may create nicks at "other" sites in the duplex (in addition to the desired cleavage site) if these possess the correct recognition sequence. This could present a problem if nicks are created in the strand it is intended to sequence rather than the strand that will be fully or partially removed to create the sequencing template and is a particular risk if the target portion of the double-stranded nucleic acid molecule is of unknown sequence.

The fact that there is no requirement for the non-natural (e.g. uracil) residue to be located in a detailed sequence context in order to provide a site for cleavage using this approach is itself advantageous. In particular, if the cleavage site is to be incorporated into an amplification primer to be used in the production of a clustered array by solid-phase amplification, it is necessarily only to replace one natural nucleotide (e.g. T) in the primer with a non-natural nucleotide (e.g. U) in order to enable cleavage. There is no need to engineer the primer to include a restriction enzyme recognition sequence of several nucleotides in length. Oligonucleotide primers including U nucleotides, and the other non-natural nucleotides listed above, can easily be prepared using conventional techniques and apparatus for chemical synthesis of oligonucleotides.

Another advantage gained by cleavage of abasic sites in a double-stranded molecule generated by action of UDG on uracil is that the first base incorporated in a "sequencing-by-synthesis" reaction initiating at the free 3' hydroxyl group formed by cleavage at such a site will always be T. Hence, if the double-stranded nucleic acid molecule forms part of a clustered array comprised of many such molecules, all of which are cleaved in this manner to produce sequencing templates, then the first base universally incorporated across the whole array will be T. This can provide a sequence-independent assay for cluster intensity at the start of a sequencing "run".

iii) Cleavage of Ribonucleotides

Incorporation of one or more ribonucleotides into a polynucleotide strand which is otherwise comprised of deoxyribonucleotides (with or without additional non-nucleotide chemical moieties, non-natural bases or non-natural backbone linkages) can provide a site for cleavage using a chemical agent capable of selectively cleaving the phosphodiester bond between a deoxyribonucleotide and a ribonucleotide or using a ribonuclease (RNAse). Therefore, sequencing templates can be produced by cleavage of one strand of a "bridged" structure at a site containing one or more consecutive ribonucleotides using such a chemical cleavage agent or an RNase. Preferably the strand to be cleaved contains a single ribonucleotide to provide a site for chemical cleavage.

Suitable chemical cleavage agents capable of selectively cleaving the phosphodiester bond between a deoxyribonucleotide and a ribonucleotide include metal ions, for example rare-earth metal ions (especially $La^{3+}$, particularly $Tm^{3+}$, $Yb^{3+}$ or $Lu^{3+}$ (Chen et al. Biotechniques. 2002, 32: 518-520; Komiyama et al. Chem. Commun. 1999, 1443-1451)), Fe(3) or Cu(3), or exposure to elevated pH, e.g. treatment with a base such as sodium hydroxide. By "selective cleavage of the phosphodiester bond between a deoxyribonucleotide and a ribonucleotide" is meant that the chemical cleavage agent is not capable of cleaving the phosphodiester bond between two deoxyribonucleotides under the same conditions.

The base composition of the ribonucleotide(s) is generally not material, but can be selected in order to optimise chemical (or enzymatic) cleavage. By way of example, rUMP or rCMP are generally preferred if cleavage is to be carried out by exposure to metal ions, especially rare earth metal ions.

The ribonucleotide(s) will typically be incorporated into one strand of a "bridged" double-stranded nucleic acid molecule (or the amplification primer from which this strand is derived if prepared by solid-phase amplification), and may be situated in a region of the bridged structure which is single-stranded when the two complementary strands of the double-stranded molecule are annealed (i.e. in a 5' overhanging portion). If the double-stranded nucleic acid molecule is prepared by solid-phase PCR amplification using forward and reverse amplification primers, one of which contains at least one ribonucleotide, the standard DNA polymerase enzymes used for PCR amplification are not capable of copying ribonucleotide templates. Hence, the PCR products will contain an overhanging 5' region comprising the ribonucleotide(s) and any remainder of the amplification primer upstream of the ribonucleotide(s).

The phosphodiester bond between a ribonucleotide and a deoxyribonucleotide or between two ribonucleotides may also be cleaved by an RNase. Any endocytic ribonuclease of appropriate substrate specificity can be used for this purpose. If the ribonucleotide(s) are present in a region which is single-stranded when the two complementary strands of the double-stranded molecule are annealed (i.e. in a 5' overhanging portion), then the RNase will be an endonuclease which has specificity for single strands containing ribonucleotides. For cleavage with ribonuclease it is preferred to include two or more consecutive ribonucleotides, and preferably from 2 to 10 or from 5 to 10 consecutive ribonucleotides. The precise sequence of the ribonucleotides is generally not material, except that certain RNases have specificity for cleavage after certain residues. Suitable RNases include, for example, RNaseA, which cleaves after C and U residues. Hence, when cleaving with RNaseA the cleavage site must include at least one ribonucleotide which is C or U.

Polynucleotides incorporating one or more ribonucleotides can be readily synthesised using standard techniques for oligonucleotide chemical synthesis with appropriate ribonucleotide precursors. If the double-stranded nucleic acid molecule is prepared by solid-phase nucleic acid amplification, then it is convenient to incorporate one or more ribonucleotides into one of the primers to be used for the amplification reaction.

iv) Photochemical Cleavage

The term "photochemical cleavage" encompasses any method which utilises light energy in order to achieve cleavage of one or both strands of the double-stranded nucleic acid molecule.

A site for photochemical cleavage can be provided by a non-nucleotide chemical spacer unit in one of the strands of the double-stranded molecule (or the amplification primer from which this strand is derived if prepared by solid-phase amplification). Suitable photochemical cleavable spacers include the PC spacer phosphoramidite (4-(4,4'-Dimethoxytrityloxy)butyramidomethyl)-1-(2-nitrophenyl)-ethyl]-2-cyanoethyl-(N,N-diisopropyl)-phosphoramidite) supplied by Glen Research, Sterling, Va., USA (cat number 10-4913-XX) which has the structure:

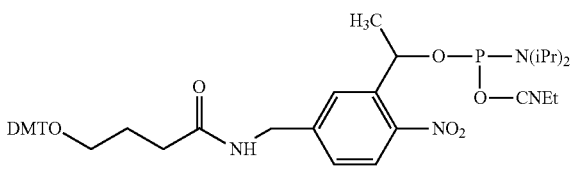

The spacer unit can be cleaved by exposure to a UV light source.

This spacer unit can be attached to the 5' end of a polynucleotide, together with a thiophosphate group which permits attachment to a solid surface, using standard techniques for chemical synthesis of oligonucleotides. Conveniently, this spacer unit can be incorporated into a forward or reverse amplification primer to be used for synthesis of a photocleavable double-stranded nucleic acid molecule by solid-phase amplification.

v) Cleavage of Hemimethylated DNA

Site-specific cleavage of one strand of a double-stranded nucleic acid molecule may also be achieved by incorporating one or more methylated nucleotides into this strand and then cleaving with an endonuclease enzyme specific for a recognition sequence including the methylated nucleotide(s).

The methylated nucleotide(s) will typically be incorporated in a region of one strand of the double-stranded nucleic acid molecule having a complementary stretch of non-methylated deoxyribonucleotides on the complementary strand, such that annealing of the two strands produces a hemimethylated duplex structure. The hemimethylated duplex may then be cleaved by the action of a suitable endonuclease. For the avoidance of doubt, enzymes which cleave such hemimethylated target sequences are not to be considered as "restriction endonucleases" excluded from the scope of the second aspect of the invention, but rather are intended to form part of the subject-matter of the invention.

Polynucleotides incorporating one or methylated nucleotides may be prepared using standard techniques for automated DNA synthesis, using appropriately methylated nucleotide precursors. If the double-stranded nucleic acid molecule is prepared by solid-phase nucleic acid amplification, then it is convenient to incorporate one or more methylated nucleotides into one of the primers to be used for the amplification reaction.

vi) PCR Stoppers

In another embodiment of the invention the double-stranded nucleic acid may be prepared by solid-phase amplification using forward and reverse primers, one of which contains a "PCR stopper". A "PCR stopper" is any moiety (nucleotide or non-nucleotide) which prevents read-through of the polymerase used for amplification, such that it cannot copy beyond that point. The result is that amplified strands derived by extension of the primer containing the PCR stopper will contain a 5' overhanging portion. This 5' overhang (other than the PCR stopper itself) may be comprised of naturally occurring deoxyribonucleotides, with predominantly natural backbone linkages, i.e. it may simply be a stretch of single-stranded DNA. The molecule may then be cleaved in the 5' overhanging region with the use of a cleavage reagent (e.g. an enzyme) which is selective for cleavage of single-stranded DNA but not double stranded DNA, for example mung bean nuclease.

The PCR stopper may be essentially any moiety which prevents read-through of the polymerase to be used for the amplification reaction. Suitable PCR stoppers include, but are not limited to, hexaethylene glycol (HEG), abasic sites, and any non-natural or modified nucleotide which prevents read-through of the polymerase, including DNA analogues such as peptide nucleic acid (PNA).

Stable abasic sites can be introduced during chemical oligonucleotide synthesis using appropriate spacer units containing the stable abasic site. By way of example, abasic furan (5'-O-Dimethoxytrityl-1',2'-Dideoxyribose-3'-[(2-cyanoethyl)-(N,N-diisopropyl)]-phosphoramidite) spacers commercially available from Glen Research, Sterling, Va., USA, can be incorporated during chemical oligonucleotide synthesis in order to introduce an abasic site. Such a site can thus readily be introduced into an oligonucleotide primer to be used in solid-phase amplification. If an abasic site is incorporated into either forward or reverse amplification primer the resulting amplification product will have a 5' overhang on one strand which will include the abasic site (in single-stranded form). The single-stranded abasic site may then be cleaved by the action of a suitable chemical agent (e.g. exposure to alkali) or an enzyme (e.g. AP-endonuclease VI, Shida el al. Nucleic Acids Research, 1996, Vol. 24, 4572-4576).

vii) Cleavage of Peptide Linker

A cleavage site can also be introduced into one strand of the double-stranded nucleic molecule by preparing a conjugate structure in which a peptide molecule is linked to one strand of the nucleic acid molecule (or the amplification primer from which this strand is derived if prepared by solid-phase amplification). The peptide molecule can subsequently be cleaved by a peptidase enzyme of the appropriate specificity, or any other suitable means of non-enzymatic chemical or photochemical cleavage. Typically, the conjugate between peptide and nucleic acid will be formed by covalently linking a peptide to one strand only of the double-stranded nucleic acid molecule, with the peptide portion being conjugated to the 5' end of this strand, adjacent to the point of attachment to the solid surface. If the double-stranded nucleic acid is prepared by solid-phase amplification, the peptide conjugate may be incorporated at the 5' end of one of the amplification primers. Obviously the peptide component of this primer will not be copied during PCR amplification, hence the "bridged" amplification product will include a cleavable 5' peptide "overhang" on one strand.

Conjugates between peptides and nucleic acids wherein the peptide is conjugated to the 5' end of the nucleic acid can be prepared using techniques generally known in the art. In one such technique the peptide and nucleic acid components of the desired amino acid and nucleotide sequence can be synthesised separately, e.g. by standard automated chemical synthesis techniques, and then conjugated in aqueous/organic solution. By way of example, the OPeC™ system commercially available from Glen Research is based on the "native ligation" of an N-terminal thioester-functionalized peptide to a 5'-cysteinyl oligonucleotide. Pentafluorophenyl S-benzylthiosuccinate is used in the final coupling step in standard Fmoc-based solid-phase peptide assembly. Deprotection with trifluoroacetic acid generates, in solution, peptides substituted with an N-terminal S-benzylthiosuccinyl group. O-trans-4-(N-a-Fmoc-S-tert-butylsulfenyl-1-cysteinyl)aminocyclohexyl O-2-cyanoethyl-N,N-diisopropylphosphoramidite is used in the final coupling step in standard phosphoramidite solid-phase oligonucleotide assembly. Deprotection with aqueous ammonia solution generates in solution 5'-S-tert-butylsulfenyl-L-cysteinyl functionalized oligonucleotides. The thiobenzyl terminus of the Modified Peptide is converted to the thiophenyl analogue by the use of thiophenol, whilst the Modified Oligonucleotide is reduced using the tris(carboxyethyl)phosphine. Coupling of these two intermediates, followed by the "native ligation" step, leads to formation of the Oligonucleotide-Peptide Conjugate.

The conjugate strand containing peptide and nucleic acid can be covalently attached to a solid support using any suitable covalent linkage technique known in the art which is compatible with the chosen surface. If the peptide/nucleic acid conjugate structure is an amplification primer to be used for solid-phase PCR amplification, attachment to the solid support must leave the 3' end of the nucleic acid component free.

The peptide component can be designed to be cleavable by any chosen peptidase enzyme, of which many are known in the art. The nature of the peptidase is not particularly limited, it is necessary only for the peptidase to cleave somewhere in the peptide component. Similarly, the length and amino acid sequence of the peptide component is not particularly limited except by the need to be "cleavable" by the chosen peptidase.

The length and precise sequence of the nucleic acid component is also not particularly limited, it may be of any desired sequence. If the nucleic acid component is to function as a primer in solid-phase PCR, then its length and nucleotide sequence will be selected to enable annealing to the template to be amplified.

Following the cleavage step, regardless of the method used for cleavage, the product of the cleavage reaction may be subjected to denaturing conditions in order to remove the portion(s) of the cleaved strand(s) that are not attached to the solid support. Suitable denaturing conditions will be apparent to the skilled reader with reference to standard molecular biology protocols (Sambrook et al., 2001, *Molecular Cloning, A Laboratory Manual,* 3rd Ed, Cold Spring Harbor Laboratory Press, Cold Spring Harbor Laboratory Press, NY; Current Protocols, eds Ausubel et al.).

Denaturation (and subsequent re-annealing of the cleaved strands) results in the production of a sequencing template which is partially or substantially single-stranded. A sequencing reaction may then be initiated by hybridisation of a sequencing primer to the single-stranded portion of the template.

The buffer additives and methods of the invention may be utilised in the nucleic acid sequencing methods described in WO 98/44152 and WO 00/18957, the contents of which are incorporated herein by reference. Both of these published International applications describe methods of parallel sequencing of multiple templates located at distinct locations on a solid support, and in particular sequencing of "clustered" arrays. The methods described therein, and indeed any other known method of sequencing nucleic acid clusters may be adapted according to the invention simply by including one or more antioxidants as additives in the buffer used for the detection/imaging steps.

As aforesaid, the use of antioxidant buffer additives in the detection steps has particular advantages in the context of sequencing on clustered arrays using fluorescently labelled nucleotide analogues. Nevertheless, the method of the invention may also be used in the context of sequencing templates on single molecule arrays of nucleic acid templates.

Single molecule arrays are generally formed by immobilisation of a single polynucleotide molecule at each discrete site that is detectable on the array. Single-molecule arrays comprised of nucleic acid molecules that are individually resolvable by optical means and the use of such arrays in sequencing are described, for example, in WO 00/06770. Single molecule arrays comprised of individually resolvable nucleic acid molecules including a hairpin loop structure are described in WO 01/57248. The method of the invention is suitable for sequencing template molecules on single molecule arrays prepared according to the disclosures of WO 00/06770 or WO 01/57248.

The fluorescent moiety may be attached to a nucleic acid via any suitable covalent or non-covalent linkage. For example, the fluorescent moiety may be attached to an oligonucleotide primer or probe which is hybridised to a target nucleic acid molecule.

Practical application of buffer additives of the invention may therefore extend to any nucleic acid detection technique which requires the use of fluorescent labels.

In a second aspect the invention provides a buffer for use in determining the identity of the base present in nucleotide(s) incorporated in a method of sequencing according to the first aspect of the invention or for use in detection of a fluorescent moiety incorporated in or attached to a polynucleotide molecule according to the second aspect of the invention, the buffer comprising one or more antioxidants in a concentration of at least 20 mM.

Again, the preferred antioxidants are as described in connection with the first aspect of the invention.

The buffers according to the invention will generally be of substantially similar composition to the detection/imaging buffer(s) typically used in the chosen detection/imaging technique, except for the addition of the antioxidant component(s).

The buffer may contain other reaction components such as enzymes, enzyme cofactors, dNTPS etc if the presence of these components is compatible with the particular detection/imaging technique for which the buffer is intended to be used. For methods involving nucleic acid synthesis, such as sequencing-by-synthesis, the same reaction buffer may be used for the nucleotide incorporation steps and for the detection steps, with no intermediate washing step. In this case the buffer may also comprise one or more nucleotides required for the nucleic synthesis reaction and also a suitable polymerase enzyme.

Buffers according to the invention can be supplied as liquid concentrates requiring dilution prior to use. Buffers may also be supplied in the form of buffer tablets or solid "concentrates" to be dissolved in a suitable solvent prior to use in order to form the final buffer according to the invention. Such formats may be more convenient for supply. Buffer concentrates or tablets may be supplied together with instructions setting out how the buffer is to be diluted prior to use. In the case of buffer concentrates and buffer tablets the amount of antioxidant present in the buffer refers to the amount present in the final buffer as it is correctly diluted or made up prior to use.

In a third aspect the invention provides a kit for use in a method of sequencing according to the first aspect of the invention comprising:

one or more nucleotides;

an enzyme capable of catalysing incorporation of said nucleotides into a nucleic acid strand complementary to a nucleic acid template to be sequenced; and a buffer according to the present invention or a supply of antioxidant(s) suitable for preparing a buffer according to the present invention.

The nucleotide(s) will preferably be fluorescent labelled nucleotides, as described in connection with the method of the invention. The nucleotides may be supplied in concentrated form for dilution prior to use and may be supplied in "reagent mixes" with other reaction components required for the sequencing reaction.

The enzyme may be any suitable enzyme capable of incorporating the chosen nucleotides into a nucleic acid strand. Many suitable polymerase enzymes are known in the art and are available commercially. In particular, the kit may include a modified polymerase as described in the applicant's co-pending International Patent Application PCT/GB04/003891.

The buffer according to the invention may be conveniently supplied in the kit concentrated or solid form as described above. Alternatively, the kit may simply contain a concentrated supply of antioxidant(s) to be added into a suitable detection/imaging buffer supplied by the end user prior to use.

The invention will be further understood with reference to the following non-limiting experimental examples, together with the accompanying drawings in which:

FIG. 1 illustrates the sequence of a template DNA molecule with lambdaF fragment. The sequences and primer binding sites for the primers P7, P5 and #562 are also shown.

EXAMPLE 1

Figure 2:
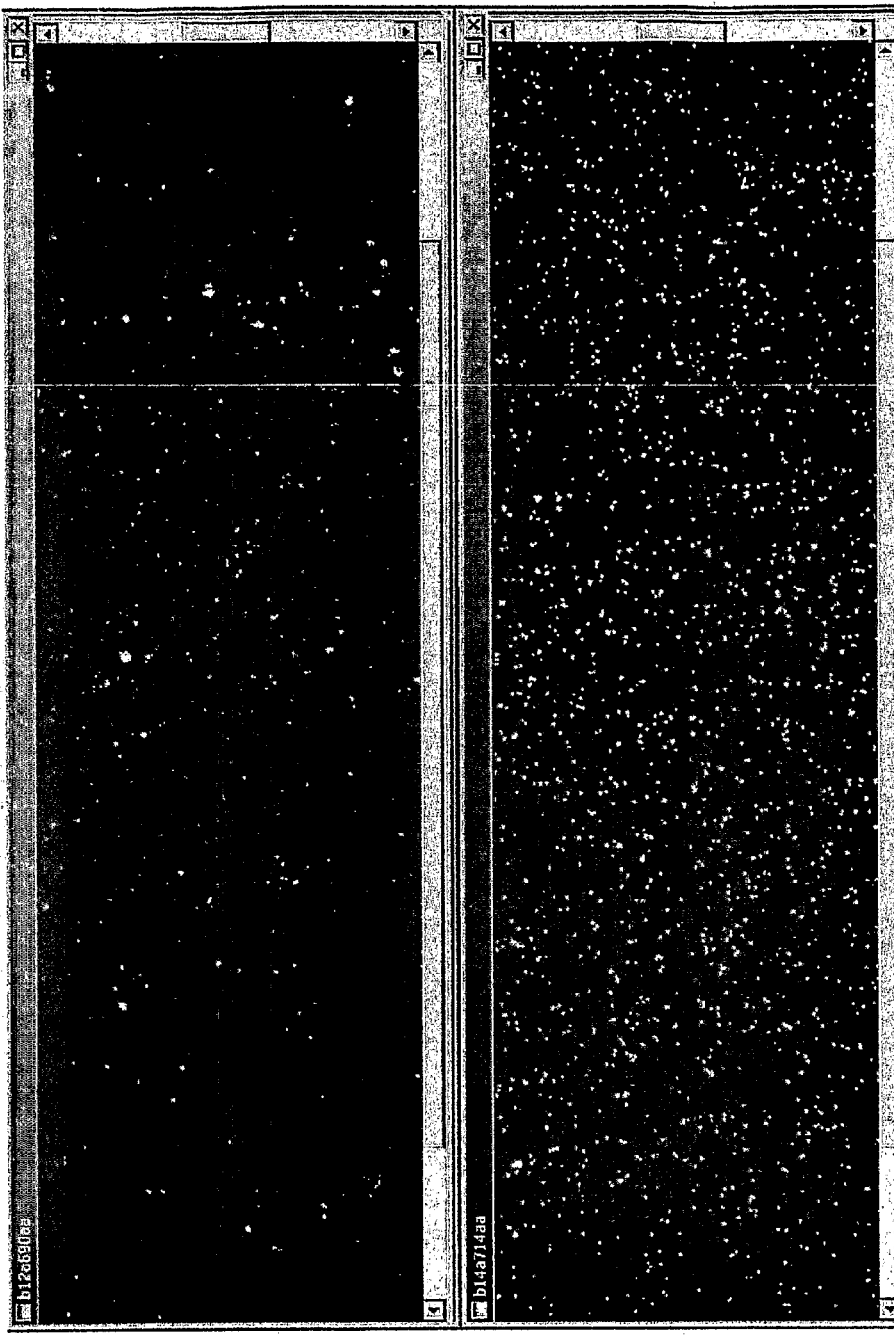
FIG. 2 shows representative fluorescent images of clustered arrays on the 7th cycle of nucleotide incorporation using imaging buffer without ascorbate (3a) or with 50 mM ascorbate (3b).

Sequencing on Arrays Prepared on Silane Coated Glass Chips

1) Formation of Nucleic Acid Clusters

Solid-phase amplification was carried out in 8 channel glass chips such as those provided by Micronit (Twente, Nederland) or IMT (Neuchâtel, Switzerland) coated with aminopropyltriethoxysilane derivatised with 1,3,5-benzenetriacetic acid (BTA). The experimental conditions and procedures are readily applicable to other solid supports.

The reaction steps of the coating procedure are summarised as follows:

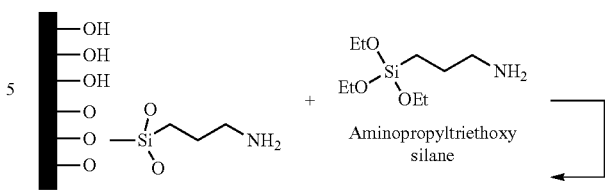

Step 1: Conversion of Glass to Amine-Terminated Glass

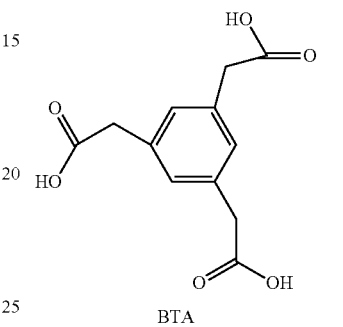

BTA

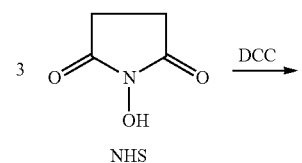

NHS

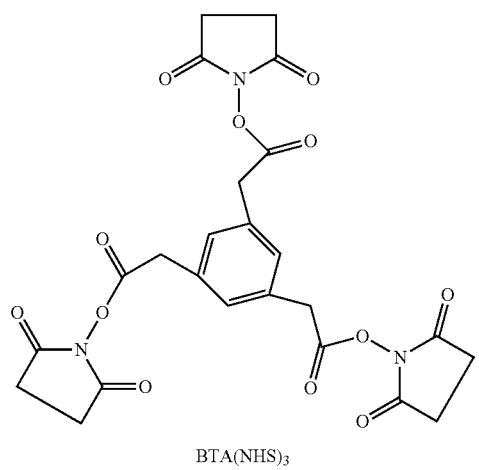

BTA(NHS)₃

Step 2: Preparation of Active Ester

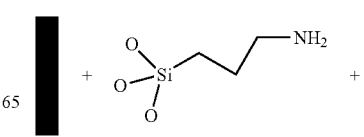

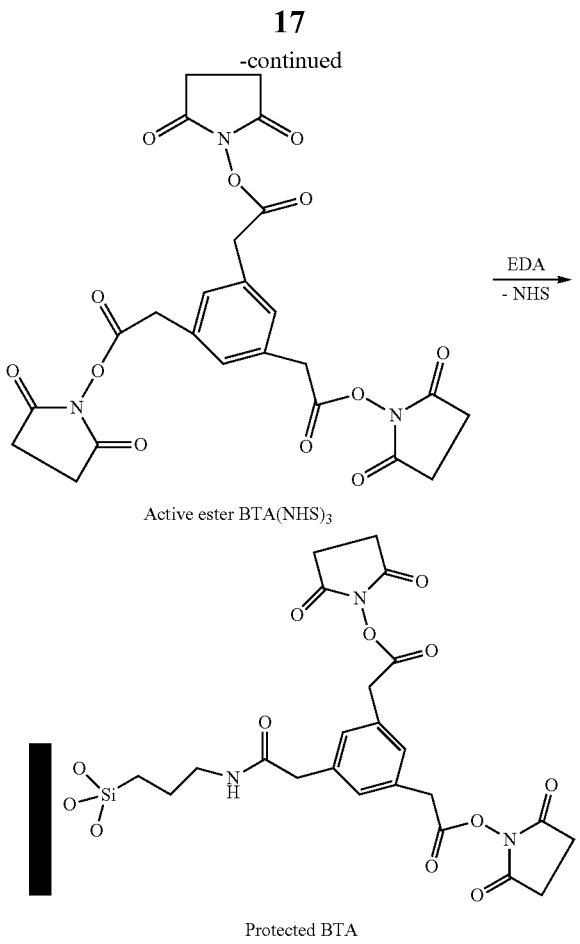

Active ester BTA(NHS)₃

Protected BTA

Step 3: Conversion of Amine-Terminated Glass to Carboxylated Glass

The 8 channel glass chips were pre-treated and silanized with 5% aminopropyltriethoxysilane, as described in the materials and methods of WO 00/18957 (incorporated herein by reference).

Ester activation of BTA was carried out by reacting the following components:

1,3,5-benzenetriacetic acid (BTA) 60.5 mg Fluka 17383
N-Hydroxysuccinimide (NHS) 99.5 mg Fluka: 56480
N,N"-Dicyclohexylcarbodiimide (DCC) 149.6 mg Fluka: 36650
N-ethyldiisopropylamine (DIEA) 41.2 ill Perkin Elmer DMF, anhydrous on molecular sieves SDS 0341021

The silanized glass channels were carboxylated by treatment with the activated BTA ester then washed with DMF, ethanol, water, 5% NaHCO₃ pH8.8 and water. The chips were dried under pure nitrogen and stored prior to use.

The BTA coated chips were grafted with P5 and P7 oligonucleotide primers in a 1:1 ratio. The sequences of the P5 and P7 primers are as shown in FIG. 1.

Grafting was carried out for 30 minutes at 50° C. in a grafting solution (70 μl per channel) containing 0.5 μM of each primer, 10 mM carbodiimide and 10 mM 1-methyl-imadazol.

Clusters of immobilized DNA were formed by amplification on a solid support substantially as described in International patent application WO 00/18957. Amplification was carried out using a lambdaF template and primers P7 and P5 as shown in FIG. 1.

2) Linearisation

This procedure implies that one of the two primers used for the generation of thermocycled DNA colonies contains a disulfide group between the amino group necessary for the binding of the primer to the surface and its first nucleotide. This disulfide bond in the P5 primer may be cleaved using Tris (2-carboxyethyl)-phosphate hydrochloride (TCEP).

Linearization was carried out at room temperature in a TCEP/Tris solution.

Aliquots of pre-weighted TCEP (about 10 mg per aliquot) are stored at 4° C. Powder must be dissolved in Tris-HCl 100 mM pH 7.5 to get a final TCEP concentration of 14.3 mg/ml (corresponding to 50 mM).

TCEP is sensitive to oxidation.

Templates to be linearised are typically exposed to TCEP/Tris for 30 minutes then washed with 0.1×SSC-0.1% Tween, then with 5×SSC.

3) Thermal Dehybridisation

Thermal denaturation or de-hybridization of the colonies was carried out in stringent buffer (TE). Temperature is ramped 0.5° C./sec to 97.5° C. and held at 97.5° C. for 2 minutes 30 seconds.

4) Hybridisation of Sequencing Primer

The procedure begins by a heating step in a stringent buffer (TE) to ensure complete denaturation of the colonies prior to hybridisation of the primer.

Hybridization was carried out in 5×SSC, using an oligonucleotide diluted to a final concentration of 500 nM. This solution should be prepared just before use, especially when fluorophore-labelled oligonucleotides are used.

Typical temperature cycling profile is as follows:
MJ-Research Thermocycler program set:
(Control method: block)
1—0.5° C./sec to 97.5° C.
2—97.5° C. for 2:30
3—97.5° C. for 0:02
  —0.1° C. per cycle
4—Go to 3 for 574 times
5—40° C. for 15:00
6—End 5) Long Read Sequencing Protocol on lamdaF Template Oligo number 562 was hybridised to the linearised clusters prepared as described above at 500 nM. Nucleotide sequences of the template and primers are shown in FIG. 1.

Sequencing was carried out using modified nucleotides prepared as described in International patent application WO 2004/018493, and labelled with four different commercially available fluorophores (Molecular Probes Inc.).

A mutant 9° N polymerase enzyme (an exo-variant including the triple mutation L408Y/Y409A/P410V and C223S) was used for the nucleotide incorporation steps.

Enzyme mix (enzymology buffer above plus 50 μg/ml YAV exo-C223S, and 1 μM each of the four labelled modified nucleotides) was applied to the clustered templates, typically for 2 min 30 s, and heated to 45° C.

Templates were maintained at 45° C. for 30 min, cooled to 20° C. and washed for 5 min with enzymology buffer, then 5 min with 5×SSC. Templates were then exposed to one of two imaging buffers: "non-ascorbate buffer" (100 mM Tris pH7.0, 30 mM NaCl), or ascorbate scan buffer (100 mM Tris pH7.0, 30 mM NaCl, 50 mM sodium ascorbate (freshly dissolved, filtered).

Templates were scanned in 4 colours.

Templates were then exposed to cycles of TCEP treatment and enzymology as follows:

TCEP Treatment
- 0.1M Tris pH 7.4 for 390 s
- Heat to 45° C.
- TCEP (100 mM in 0.1 M Tris pH 7.4) for 390 s
- Wait for 30 min, flushing for 20 s every 10 min
- Cool to 20° C.
- Enzymology buffer for 390 s
- 5×SSC buffer for 390 s
- "non ascorbate buffer" (100 mM Tris pH 7.0, 30 mM NaCl) for 330 s OR "ascorbate buffer" (100 mM Tris pH 7.0, 30 mM NaCl, 50 mM sodium ascorbate) for 330 s
- 9. Scan in 4 colours Enzymology Cycle
- Enzymology buffer for 390 s
- Heat to 45° C.
- Enzyme mix for 390 s
- Wait for 30 min, flushing for 20 s every 10 min
- Cool to 20° C.
- Enzymology buffer for 390 s
- 5×SSC buffer for 390 s
- "non ascorbate buffer" (100 mM Tris pH 7.0, 30 mM NaCl) for 330 s, scan in 4 colours
- "DMSO buffer" (100 mM Tris pH 7.0, 30 mM NaCl, 50 mM sodium ascorbate) for 330 s, scan 4 colours In total, 25 cycles of data were collected.

A clear difference between the number of clusters detected at each cycle could be seen. The non ascorbate buffer resulted in a loss of signal for each cluster, and a loss of the number of detectable clusters, such that after seven cycles the sequencing process was no longer working. Using the ascorbate buffer, at least 18 cycles of sequencing could be achieved.

The slides were scanned on a white light epifluorescence microscope set up with four separate excitation and emission channels appropriate to the fluorophores.

Representative results are illustrated in FIG. 2.

Example 2

Sequencing on Arrays Prepared on a Hydrogel Coated Glass Surface

The solid supports used in this experiment were 8-channel glass chips such as those provided by Micronit (Twente, Nederland) or IMT (Neuchatel, Switzerland). However, the experimental conditions and procedures are readily applicable to other solid supports.

Acrylamide Coating of Glass Chips

Chips were washed as follows: neat Decon for 30 min, milliQ H$_2$O for 30 min, NaOH 1N for 15 min, milliQ H$_2$O for 30 min, HCl 0.1N for 15 min, milliQ H$_2$O for 30 min.

Polymer Solution Preparation

For 10 ml of 2% polymerisation mix.
- 10 ml of 2% solution of acrylamide in milliQ H$_2$O
- 165 μl of a 100 mg/ml N-(5-bromoacetamidylpentyl) acrylamide (BRAPA) solution in DMF (23.5 mg in 235 μl DMF)
- 11.5 μl of TEMED
- 100 μl of a 50 mg/ml solution of potassium persulfate in milliQ H$_2$O (20 mg in 400 μl H$_2$O)

The 10 ml solution of acrylamide was first degassed with argon for 15 min. The solutions of BRAPA, TEMED and potassium persulfate were successively added to the acrylamide solution. The mixture was then quickly vortexed and immediately used. Polymerization was then carried out for 1 h 30 at RT. Afterwards the channels were washed with milliQ H$_2$O for 30 min. The slide are then dried by flushing argon through the inlets and stored under low pressure in a dessicator.

Synthesis of N-(5-bromoacetamidylpentyl) acrylamide (BRAPA)

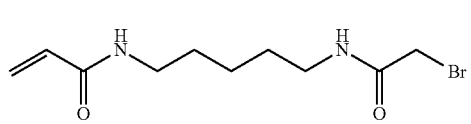

(1)

N-Boc-1,5-diaminopentane toluene sulfonic acid was obtained from Novabiochem. The bromoacetyl chloride and acryloyl chloride were obtained from Fluka. All other reagents were Aldrich products.

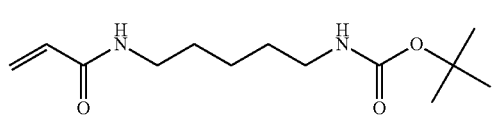

(2)

To a stirred suspension of N-Boc-1,5-diaminopentane toluene sulfonic acid (5.2 g, 13.88 mmol) and triethylamine (4.83 ml, 2.5 eq) in THF (120 ml) at 0° C. was added acryloyl chloride (1.13 ml, 1 eq) through a pressure equalized dropping funnel over a one hour period. The reaction mixture was then stirred at room temperature and the progress of the reaction checked by TLC (petroleum ether: ethyl acetate 1:1). After two hours, the salts formed during the reaction were filtered off and the filtrate evaporated to dryness. The residue was purified by flash chromatography (neat petroleum ether followed by a gradient of ethyl acetate up to 60%) to yield 2.56 g (9.98 mmol, 71%) of product 2 as a beige solid. $^1$H NMR (400 MHz, d$_6$-DMSO): 1.20-1.22 (m, 2H, CH$_2$), 1.29-1.43 (m, 13H, tBu, 2×CH$_2$), 2.86 (q, 2H, J=6.8 Hz and 12.9 Hz, CH$_2$), 3.07 (q, 2H, J=6.8 Hz and 12.9 Hz, CH$_2$), 5.53 (dd, 1H, J=2.3 Hz and 10.1 Hz, CH), 6.05 (dd, 1H, J=2.3 Hz and 17.2 Hz, CH), 6.20 (dd, 1H, J=10.1 Hz and 17.2 Hz, CH), 6.77 (t, 1H, J=5.3 Hz, NH), 8.04 (bs, 1H, NH). Mass (electrospray+) calculated for C$_{13}$H$_{24}$N$_2$O$_3$ 256. found 279 (256+Na$^+$).

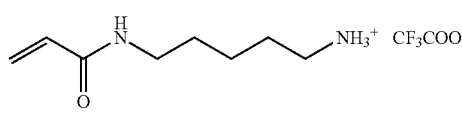

(3)

Product 2 (2.56 g, 10 mmol) was dissolved in trifluoroacetic acid:dichloromethane (1:9, 100 ml) and stirred at room temperature. The progress of the reaction was monitored by TLC (dichloromethane:methanol 9:1). On completion, the reaction mixture was evaporated to dryness, the residue co-evaporated three times with toluene and then purified by flash chromatography (neat dichloromethane followed by a gradient of methanol up to 20%). Product 3 was obtained as a white powder (2.43 g, 9 mmol, 90%). $^1$H NMR (400 MHz, D$_2$O): 1.29-1.40 (m, 2H, CH$_2$), 1.52 (quint., 2H, J=7.1 Hz, CH$_2$), 1.61 (quint., 2H, J=7.7 Hz, CH$_2$), 2.92 (t, 2H, J=7.6 Hz, CH$_2$), 3.21 (t, 2H, J=6.8 Hz, CH$_2$), 5.68 (dd, 1H, J=1.5 Hz and 10.1

Hz, CH), 6.10 (dd, 1H, J=1.5 Hz and 17.2 Hz, CH), 6.20 (dd, 1H, J=10.1 Hz and 17.2 Hz, CH). Mass (electrospray+) calculated for $C_8H_{16}N_2O$, 156. found 179 (156+Na$^+$).

To a suspension of product 3 (6.12 g, 22.64 mmol) and triethylamine (6.94 ml, 2.2 eq) in THF (120 ml) was added bromoacetyl chloride (2.07 ml, 1.1 eq), through a pressure equalized dropping funnel, over a one hour period and at −60° C. (cardice and isopropanol bath in a dewar). The reaction mixture was then stirred at room temperature overnight and the completion of the reaction was checked by TLC (dichloromethane:methanol 9:1) the following day. The salts formed during the reaction were filtered off and the reaction mixture evaporated to dryness. The residue was purified by chromatography (neat dichloromethane followed by a gradient of methanol up to 5%). 3.2 g (11.55 mmol, 51%) of the product 1 (BRAPA) were obtained as a white powder. A further recrystallization performed in petroleum ether:ethyl acetate gave 3 g of the product 1. $^1$H NMR (400 MHz, d$_6$-DMSO): 1.21-1.30 (m, 2H, CH$_2$), 1.34-1.48 (m, 4H, 2×CH$_2$), 3.02-3.12 (m, 4H, 2×CH$_2$), 3.81 (s, 2H, CH$_2$), 5.56 (d, 1H, J=9.85 Hz, CH), 6.07 (d, 1H, J=16.9 Hz, CH), 6.20 (dd, 1H, J=10.1 Hz and 16.9 Hz, CH), 8.07 (bs, 1H, NH), 8.27 (bs, 1H, NH). Mass (electrospray+) calculated for $C_{10}H_{17}BrN_2O_2$ 276 or 278. found 279 (278+H$^+$), 299 (276+Na$^+$).

Grafting of Primers

The primers were 5'-phosphorothioate oligonucleotides. Grafting was carried out using 80 μl per channel in 10 mM phosphate buffer pH7 for 1 h at RT with the following two oligonucleotides each at a concentration of 0.5 μM.

```
P7 non-cleavable primer (supplied by Eurogentec):
5'-phosphorothioate-TTTTTTTTTCAAGCAGAAGACGGCATAC
GA-3'OH P5 cleavable primer (supplied by ATD):
5'-phosphorothioate-TTTTTTTTT-(diol)X3-AATGATACG
GCGACCACCGA-3'OH
```

The structure of the diol linker incorporated into the cleavable primer was as follows:

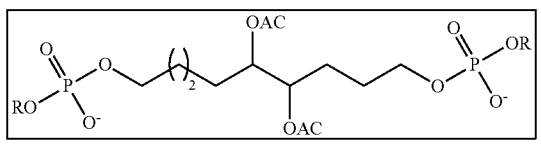

The channels are washed with 10 mM phosphate buffer, followed by 10 mM Tris/10 mM EDTA pH 8.0 (100 μL per channel) to remove unbound DNA.

Colony Formation

An amplification template may be hybridised to the grafted primers immediately prior to the amplification reaction. The amplification reaction thus begins with an initial primer extension step rather than template denaturation. Amplification was carried out using a lambdaF template and primers P7 and P5 as shown in FIG. 1.

The hybridization procedure begins with a heating step in a stringent buffer (95° C. for 5 minutes in TE) to ensure complete denaturation prior to hybridisation of the template. Hybridization was then carried out in 5×SSC, using template diluted to the desired final concentration. After the hybridization, the chip was washed for 5 minutes with milliQ water to remove salts.

Surface amplification was carried out in an MJ Research thermocycler.

A typical program is as follows:
1—97.5° C. for 0:45
2—X° C. for 1:30
3—73° C. for 1:30
4—Go to 1 [40] times
5—73° C. for 5:00
6—20° C. for 3:00
7—End Since the first step in the amplification reaction was extension of the primers bound to template in the initial hybridisation step the first denaturation and annealing steps of this program are omitted (i.e. the chip is placed on the heating block only when the amplification mix is pumped through the flow cell and the temperature is at 73° C.)

The annealing temperature (X° C., step 2) depends on the primer pair that is used. Experiments have determined an optimal annealing temperature of 57° C. for P5/P7 primers. For other primer-pairs the optimum annealing temperature can be determined by experiment. The number of cycles may be varied if required.

Amplification was carried out in a reaction solution comprising 1×PCR reaction buffer (supplied with the enzyme) 1M betain, 1.3% DMSO, 200 μM dNTPs and 0.025 U/μL Taq polymerase.

General features of the solid-phase amplification procedure to produce nucleic acid colonies are as described in International patent applications WO 98/44151 and WO 00/18957.

Linearisation

Channels to be cleaved were treated with a solution of 0.1M of sodium periodate and 0.1M ethanolamine in water for 1 hour at room temperature. All channels were then washed for 30 minutes with milliQ water at room temperature.

Thermal Dehybridisation

Thermal denaturation or de-hybridization of linearised colonies was carried out in stringent buffer (TE). Temperature was ramped 0.5° C./sec to 97.5° C. and held at 97.5° C. for 2 minutes 30 seconds.

Hybridisation of Sequencing Primer

The procedure begins with a heating step in a stringent buffer (TE) to ensure complete denaturation of the colonies prior to hybridisation of the primer.

Hybridization was carried out in 5×SSC, using an oligonucleotide diluted to a final concentration of 500 nM.

Typical temperature cycling profile was as follows:
MJ-Research Thermocycler program set:
(Control method: block)
1—0.5° C./sec to 97.5° C.
2—97.5° C. for 2:30
3—97.5° C. for 0:02
   —0.1° C. per cycle
4—Go to 3 for 574 times
5—40° C. for 15:00
6—End 5) Long Read Sequencing Protocol on lamdaF Template Oligo number 562 was hybridised to the linearised clusters prepared as described above at 500 nM. Nucleotide sequences of the template and primers are shown in FIG. 1.

Sequencing was carried out using modified nucleotides prepared as described in International patent application WO 2004/018493, and labelled with four different commercially available fluorophores (Molecular Probes Inc.).

A mutant 9° N polymerase enzyme (an exo-variant including the triple mutation L408Y/Y409A/P410V and C223S) was used for the nucleotide incorporation steps.

Enzyme mix (enzymology buffer (50 mM Tris-HCl pH 8.0, 6 mM MgSO4, 1 mM EDTA, 0.05% (v/v) Tween-20) plus 50 μg/ml YAV exo-C223S, and 1 μM each of the four labelled modified nucleotides) was applied to the clustered templates, typically for 2 min 30 s, and heated to 45° C.

Templates were maintained at 45° C. for 30 min, cooled to 20° C. and washed for 5 min with enzymology buffer, then 5 min with 5×SSC. Templates were then exposed to one of two imaging buffers: "non-ascorbate buffer" (100 mM Tris pH7.0, 30 mM NaCl), or ascorbate scan buffer (100 mM Tris pH7.0, 30 mM NaCl, 50 mM sodium ascorbate (freshly dissolved, filtered).

Templates were scanned in 4 colours.

Templates were then exposed to cycles of TCEP treatment and enzymology as follows:

TCEP Treatment
- 0.1M Tris pH 7.4 for 390 s
- Heat to 45° C.
- TCEP (100 mM in 0.1 M Tris pH 7.4) for 390 s
- Wait for 30 min, flushing for 20 s every 10 min
- Cool to 20° C.
- Enzymology buffer for 390 s
- 5×SSC buffer for 390 s
- "non ascorbate buffer" (100 mM Tris pH 7.0, 30 mM NaCl) for 330 s OR "ascorbate buffer" (100 mM Tris pH 7.0, 30 mM NaCl, 50 mM sodium ascorbate) for 330 s
- 9. Scan in 4 colours Enzymology Cycle
- Enzymology buffer for 390 s
- Heat to 45° C.
- Enzyme mix for 390 s
- Wait for 30 min, flushing for 20 s every 10 min
- Cool to 20° C.
- Enzymology buffer for 390 s
- 5×SSC buffer for 390 s
- "non ascorbate buffer" (100 mM Tris pH 7.0, 30 mM NaCl) for 330 s, scan in 4 colours
- "DMSO buffer" (100 mM Tris pH 7.0, 30 mM NaCl, 50 mM sodium ascorbate) for 330 s, scan 4 colours In total, 25 cycles of data were collected.

A clear difference between the number of clusters detected at each cycle could be seen. The non ascorbate buffer resulted in a loss of signal for each cluster, and a loss of the number of detectable clusters, such that after seven cycles the sequencing process was no longer working. Using the ascorbate buffer, at least 18 cycles of sequencing could be achieved.

The slides were scanned on a white light epifluorescence microscope set up with four separate excitation and emission channels appropriate to the fluorophores.

Representative results were substantially similar to those illustrated in FIG. 2, demonstrating a clear improvement in brightness in the presence of ascorbate.

The invention claimed is:

1. A method of sequencing at least two nucleotides of a template nucleic acid comprising repeating the steps of:
   a) incorporating one or more fluorescently labelled nucleotides into a strand of nucleic acid complementary to said template nucleic acid; and
   b) determining the identity of one or more of the incorporated nucleotide(s) wherein the steps of determining the identity of the incorporated nucleotide(s) is carried out in a buffer which comprises ascorbic acid, or a salt thereof;
   wherein at least 10 nucleotides are incorporated and the identity of the base present in each of the incorporated nucleotides is determined.

2. The method of claim 1, wherein the method comprises a method of inhibiting light-induced degradation of nucleic acids during a detection step of a nucleic acid sequencing reaction comprising the steps of:
   a) incorporating one or more fluorescently labelled nucleotides into a strand of nucleic acid complementary to a template nucleic acid immobilized to a solid support;
   b) irradiating said template nucleic acid in the presence of a detection buffer comprising ascorbic acid, or a salt thereof;
   c) removing the fluorescent label from the incorporated nucleotide(s) using a chemical treatment; and
   d) washing said solid support;
   wherein steps a-d are repeated at least 10 times.

3. The method according to claim 2, wherein said fluorescently labelled nucleotide is a nucleotide triphosphate.

4. The method according to claim 2, wherein the ascorbic acid or salt thereof is present in the buffer at a concentration of at least 10 mM.

5. The method according to claim 2, wherein the ascorbic acid or salt thereof is present in the buffer at a concentration of at least 20 mM.

6. The method according to claim 2, wherein the ascorbic acid or salt thereof is present in the buffer at a concentration of up to 100 mM.

7. The method according to claim 2, wherein the salt of ascorbic acid is sodium ascorbate.

8. The method according to claim 2, wherein the buffer further comprises additional antioxidants.

9. The method according to claim 2, wherein the buffer has a pH of about 5.5 to about 8.6.

10. The method according to claim 2, wherein the buffer has a pH of about 7.

11. The method according to claim 2, wherein the template nucleic acid is present in an array.

12. The method according to claim 11, wherein the array is a clustered array.

13. The method according claim 2, wherein steps a-d are repeated at least 16 times.

14. The method according to claim 2, wherein said fluorescent label is attached to the one or more of the incorporated nucleotide(s) via a linker comprising a disulfide linkage.

15. The method according to claim 2, wherein said fluorescent label is attached to the one or more of the incorporated nucleotide(s) via a linker comprising an azide.

\* \* \* \* \*